Figure 1:
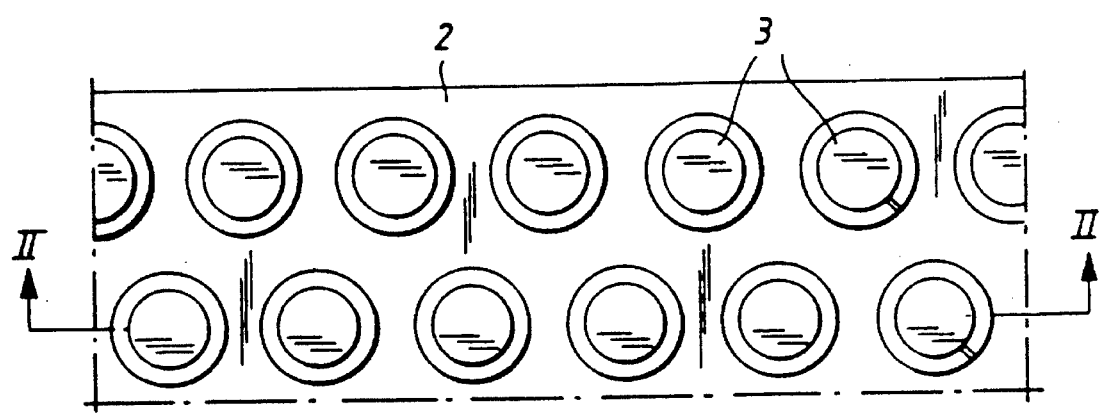

United States Patent [19]

Billgren

[11] Patent Number: 5,546,960
[45] Date of Patent: Aug. 20, 1996

[54] SURGICAL DRAPE

[75] Inventor: Tomas Billgren, Kullavik, Sweden

[73] Assignee: Molnlycke AB, Goteborg, Sweden

[21] Appl. No.: 362,441

[22] PCT Filed: Jun. 30, 1993

[86] PCT No.: PCT/SE93/00603

§ 371 Date: Dec. 29, 1994

§ 102(e) Date: Dec. 29, 1994

[87] PCT Pub. No.: WO94/01051

PCT Pub. Date: Jan. 20, 1994

[30] Foreign Application Priority Data

Jul. 8, 1992 [SE] Sweden ................................. 9202117

[51] Int. Cl.⁶ .................................................. A61B 19/00
[52] U.S. Cl. ............................................................ 128/849
[58] Field of Search ...................... 128/849–856

[56] References Cited

U.S. PATENT DOCUMENTS

| | | | |
|---|---|---|---|
| 3,602,220 | 8/1971 | Bunyan . | |
| 3,667,458 | 6/1972 | Krebs | 128/853 |
| 3,921,627 | 11/1975 | Wilson | 128/853 |
| 4,204,532 | 5/1980 | Lind | 128/849 |
| 4,379,192 | 4/1983 | Wahlguist | 128/853 |
| 4,873,997 | 10/1989 | Marshall | 128/849 |
| 5,151,314 | 9/1992 | Brown | 128/849 |
| 5,222,507 | 6/1993 | Taylor | 128/849 |
| 5,386,835 | 2/1995 | Elphick | 128/849 |

*Primary Examiner*—Michael A. Brown
*Attorney, Agent, or Firm*—Young & Thompson

[57] ABSTRACT

The present invention relates to a surgical drape includes an absorbent sheet (1) and a fluid-impermeable sheet (2) attached thereto. According to the invention, the fluid-impermeable sheet (2) is provided with projections (3) on that side which lies distal from the absorbent sheet (1).

7 Claims, 1 Drawing Sheet

SURGICAL DRAPE

The present invention relates to a surgical drape comprised of an absorbent sheet and a fluid-impermeable sheet attached thereto.

Applicant retails a surgical drape under the designation Klinidrape® (registered trademark), which is comprised of a three-sheet laminate. The laminate comprises a liquid-absorbent top sheet made of nonwoven material, a fluid-impermeable intermediate sheet of polyethylene, and a bottom absorbent sheet of cellulose wadding. The purpose of the top sheet is to absorb blood and other fluids delivered from the surgical wound, so as to prevent contamination of theatre personnel and the operating theatre as a whole. The plastic film forms a barrier against the transportation of fluid-carried bacteria between the patient and the area of the surgical wound, while the layer of cellulose wadding on the underneath of the drape is intended to enhance patient comfort, by absorbing perspiration and preventing direct contact of the patient's skin with the plastic sheet.

Although Klinidrape® fulfills the requirements of a surgical drape in a highly satisfactory fashion, the drape cannot be readily arranged in folds because of its relatively complicated structure, and is felt to be less soft than those surgical drapes of textile material traditionally replaced by this drape.

The object of the invention is to provide a surgical drape of simpler construction which has equally as good properties as or better properties than Klinidrape® with respect to both the absorbency of the top sheet and the barrier function of and the patient comfort afforded by the drape, and which can be arranged in folds more easily than the known drape.

This object is achieved in accordance with the invention with a surgical drape of the kind defined in the introduction which is characterized in that the fluid-impermeable sheet is provided with projections on that side of the drape which lies distal to the absorbent sheet. Similar to Klinidrape®, such a surgical drape has absolute barrier properties. Furthermore, such a surgical drape will provide good patient comfort, because only the bottoms of the projections will lie against the patient's skin, thereby providing good air circulation between the skin and the drape.

According to one advantageous embodiment, the projections are cup-shaped. This enhances the absorbency of the top sheet, in that fluid delivered by the surgical wound will be collected and held in the cup-shaped cavities of the projections.

According to a further embodiment of the invention, the absorbent sheet is comprised of nonwoven spunlace material and the fluid-impermeable sheet is comprised of polyethylene film. In a preferred variant, the fluid-impermeable sheet is air-permeable, which in the preferred embodiment is achieved by using plastic film which is microporous.

Figure 2:
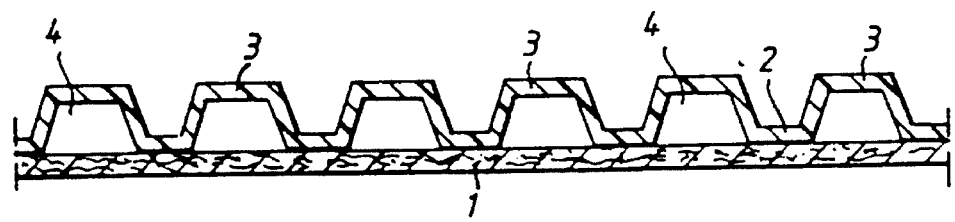

An exemplifying embodiment of the invention will now be described with reference to the accompanying drawing, in which FIG. 1 is a bottom view of part of a surgical drape constructed in accordance with one embodiment of the invention; and FIG. 2 is a cross-sectional view taken on the line II—II in FIG. 1.

The illustrated surgical drape is comprised of an absorbent top sheet 1 and a bottom fluid-impermeable sheet 2 which when the drape is used lies nearest the patient's skin. The top sheet 1 is preferably made of a nonwoven material and may advantageously be made of spunlace material, which because it can be stretched coacts remarkably well with the plastic film, e.g. the polyethylene film of which the bottom fluid-impermeable barrier sheet 2 is preferably comprised. The strength of spunlace material will enable the top sheet to provide all the strength that is required of the drape, thereby obviating the need for the plastic film to take-up any appreciable load.

The whole of the undersurface of the plastic film 2 is provided with cup-shaped projections 3. This greatly reduces the abutment surface of the plastic film with the skin, since it is only the bottoms of the projections which come into contact with the patient's skin when the drape is in use. Furthermore, air is able to circulate between the projections on the undersurface of the drape and the drape is there felt to be very comfortable by the patient. Patient comfort can be further enhanced when the plastic film used is microporous, i.e. fluid-impervious but air-permeable.

Each projection 3 contains a cavity or space 4 in which fluid delivered by the surgical wound is able to collect. The inventive surgical drape has thus a much greater absorbency than the Klinidrape®.

A surgical drape of the aforedescribed kind is conveniently manufactured by extruding the plastic material directly onto a roll or cylinder which has cup-shaped, air-permeable moulds disposed over the whole of its peripheral surface, and by then subjecting the undersides of said moulds to strong subpressure, thereby vacuum-shaping the projections on the plastic film. Nonwoven material is applied to the plastic film immediately after forming the projections and prior to the plastic film having cooled (it may be necessary to subject the plastic film to a supplementary heating process) and thus joined with the parts of the plastic film that lie outside the projections.

It will be understood that the projections may have forms other than the truncated conical forms shown in FIGS. 1 and 2. For instance, the projections may have a hemispherical or part-spherical shape, a pyramidal shape, a cylindrical shape, a cubic shape, etc. In those cases when the increase of patient comfort that accompanies a decrease in the abutment surface with the skin and improved air-circulation will suffice, the projections need not necessarily be hollow, i.e. have a cup-shaped cavity to increase the absorbency of the drape, although such projections are preferred.

It will also be understood that the projections can be arranged in patterns other than the pattern illustrated in FIG. 1, and neither need the projections extend over the whole surface of the drape. Instead, the projections can be provided over separate parts of the drape, with a pattern of projections separated by parts which lack projections. It is preferred, however, that the pattern of projections will extend over essentially the whole of the drape area. One exception is found in those parts of the drape which are intended to be fastened to the patient's skin and are provided with an adhesive to this end. In order to achieve a more secure bond between the two sheets of the drape in the aforesaid parts, these parts will preferably be devoid of projections. This will enable a stronger adhesive to be used without risk of breaking the bond between the sheets of the drape when removing the drape from the patient. Since these parts of the drape are applied around the wound area, this will reduce the risk of wound fluid running or seeping in beneath the drape. In those surgical drape systems that are at present generally used, those parts of the edge portions of the drape or the peripheral region around a recess in the drape that are provided with an adhesive are adapted for particular surgical operations.

Thus, the invention provides a surgical drape which despite being of simpler construction than the Klinidrape® has equally as good functional properties, or even better functional properties than the Klinidrape® and can be arranged in folds more easily than the Klinidrape®, due to the fact that it is comprised solely of two sheets.

I claim:

1. A surgical drape which is comprised of an absorbent top sheet (1) and attached thereto a fluid-impermeable bottom sheet (2) forming a barrier against fluid transfer between the two sides of the sheet, the fluid-impermeable sheet (2) having projections (3) on the underside thereof that in use lies nearest the user's skin.

2. A surgical drape according to claim 1, wherein the projections (3) are cup-shaped.

3. A surgical drape according to claim 1, wherein the absorbent sheet (1) is made of a nonwoven material.

4. A surgical drape according to claim 3, wherein the nonwoven material (1) is a spunlace material.

5. A surgical drape according to claim 1, wherein the fluid-impermeable sheet (2) is comprised of plastic film.

6. A surgical drape according to claim 5, wherein the plastic film (2) is comprised of polyethylene.

7. A surgical drape according to claim 1, wherein the fluid-impermeable sheet (2) is air-permeable.

* * * * *